United States Patent [19]

Blem et al.

[11] Patent Number: 4,919,703

[45] Date of Patent: Apr. 24, 1990

[54] METHOD OF STIMULATING THE GROWTH OF PLANTS EMPLOYING SUBSTITUTED OXADIAZOLES

[75] Inventors: Allen R. Blem, Cheshire; Howard L. Plant, Milford; Richard R. Regis, Harwinton, all of Conn.

[73] Assignee: Uniroyal Chemical Company, Inc., Middlebury, Conn.

[21] Appl. No.: 234,439

[22] Filed: Aug. 19, 1988

[51] Int. Cl.$^5$ ...................... A01N 43/82; A01N 57/16
[52] U.S. Cl. ........................................... 71/86; 71/87; 71/90; 71/92
[58] Field of Search .......................... 71/92, 86, 87, 90

[56] References Cited

U.S. PATENT DOCUMENTS

| | | | |
|---|---|---|---|
| 4,035,175 | 7/1977 | Brouwer et al. | 71/76 |
| 4,210,762 | 7/1980 | Howe | 548/145 |
| 4,654,330 | 3/1987 | Plant et al. | 514/89 |

FOREIGN PATENT DOCUMENTS 708460  12/1970  South Africa .

OTHER PUBLICATIONS

Japanese Patent Publication 57-188503 with Translation.
Belgian Pat. 816,774.
Japanese Patent Publication 57188-503, Chem. Abstr. 98, 121365e (1982).
German Pat. No. 2,600,655, Chem. Abstr. 85, 155072d (1976).

*Primary Examiner*—Richard L. Raymond
*Attorney, Agent, or Firm*—Glenn E. Karta

[57] ABSTRACT

A method of stimulating the growth of desirable plants comprising applying a plant growth stimulatory amount of certain 2-methylhalide or 2-methylthiophosphate substituted 1,3,4-oxadiazole compounds.

3 Claims, No Drawings ced
METHOD OF STIMULATING THE GROWTH OF PLANTS EMPLOYING SUBSTITUTED OXADIAZOLES

FIELD OF THE INVENTION

This invention is directed to a method of stimulating the growth of plants, which method involves the application of a plant growth stimulatory effective amount of at least one member of a class of substituted oxadiazole compounds.

BACKGROUND OF THE INVENTION

The modification and/or regulation of plant growth to provide beneficial effects is well appreciated by those in the agricultural art. Among the most well recognized classes of plant growth regulatory chemicals are plant growth stimulants. Plant growth stimulants can result in a number of biological manifestations including the stimulation of the extensive growth of intact plants; the germination of dormant seeds and the growth of dormant buds; the overcoming of the light requirement for flowering (in certain species); the overcoming of the requirement in certain species for vernalization for flowering; the stimulation of the mobilization of foods and minerals in seed storage cells; the causing of parthenocarpic fruit development, as well as the delaying of aging in leaves and citrus fruits.

The commercial application of plant growth stimulants has involved the treatment of a wide variety of species to effect a number of beneficial changes. Thus, these types of compounds have been applied to fruits such as pears, lemons, grapes and cherries to increase the size and/or amount of fruit developed; to vegetables such as asparagus, celery and lettuce to promote vegetative growth; to seeds of crops such as oats, peas, cotton, rye, soybeans and wheat to promote rapid emergence; and to ornamentals to produce earlier blooming or more profuse or larger flowering.

However, there are drawbacks associated with many of the plant growth stimulants, such as gibberellins (a naturally occuring product of the Gibberella fungus, this class of compounds also being found in higher plants) including high costs, detrimental "side effects", short duration of effect, and the like. Accordingly, it would be desirable to possess new compounds which would function as plant growth stimulants and which would overcome one or more of the shortcomings of presently employed plant growth regulants.

The use of 1,3,4-oxadiazoles as pesticides is known in the art. Thus, U.S. Pat. No. 4,654,330 to Plant et al shows that certain of the substituted 1,3,4-oxadiazoles employed in the method of this invention are active as insecticides, nematocides and acaricides. Somewhat similarly, South African patent application Ser. No. 708,460 shows dithiophosphate substituted-1,3,4-oxadiazoles which are active as acaricides. However, neither of these patents suggests or discloses that the compounds disclosed therein would exhibit plant growth stimulatory activity.

Moreover, there have been several disclosures in the past that certain 1,3,4-oxadiazoles exhibit plant growth regulatory activity of the stunting or dwarfing variety. Thus, Belgian Pat. No. 816,774 shows (1,1,3,3-tetrahaloethyl)-5-amino-1,3,4-oxadiazoles which are valuable for dwarfing barley, while U.S. Pat. No. 4,035,175 to Brouwer et al shows 2-(1,3,4-oxadiazol-2-yl) benzoic acids and derivatives thereof, the application of which will lead to dwarfing and cessation of terminal growth. Similarly, U.S. Pat. No. 4,210,762 to Howe shows 2,5-di(substituted)phenyl-1,3,4-oxadiazoles which result in stature reduction, while U.S. Pat. No. 4,259,104 shows certain 4- and 5-substituted 2-(aryloxymethyl)-1,3,4-oxadiazoles which exhibit plant growth retardation activity.

Plant growth regulatory activity has also been reported for various 1,2,4-oxadiazoles. Thus, U.S. Pat. No. 4,135,910 to Howe shows 1,2,4-oxadiazol-3-yl-benzoates which are useful as growth regulants while Japanese Patent Publication No. 57188-503 shows a 1,2,4-oxadiazolyl chlorobenzene compound which functions as a plant growth stimulant. Somewhat similarly, German Pat. No. 2,600,655 discloses a variety of diphenyl-substituted heterocyclic compounds, including oxadiazolyl compounds, which exhibit inhibitory plant growth regulatory activity.

Thus, it is completely unexpected that the 1,3,4-oxadiazole compounds could be found which would exhibit plant growth stimulatory activity.

DESCRIPTION OF THE INVENTION

The present invention is directed to a method for stimulating the growth of desirable plants, which method comprises applying to plants an effective plant growth stimulatory amount of a compound having the structural formula:

$$R-\underset{O}{\overset{N-N}{\underset{\|}{\bigvee}}}-\underset{CH-R^2}{\overset{R^1}{|}} \quad (I)$$

wherein:
R is
  $C_1-C_{12}$ alkyl,
  $C_3-C_6$ cycloalkyl,
  $C_3-C_6$ cycloalkyl substituted with one or more members selected from the group consisting of halogen and $C_1-C_3$ alkyl,
  allyl,
  $C_3-C_5$ alkoxycarbonylmethyl,
  $C_7-C_9$ aralkyl,
  styryl,
  phenyl,
  naphthyl,
  furanyl,
  pyridyl,
  thienyl,
  phenyl substituted with halogen, $C_1-C_4$ alkyl, trihalomethyl, $C_1-C_4$ alkoxy, trihalomethoxy, trihalomethylthio, $C_1-C_4$ alkylthio, phenyl, phenoxy, cyano or nitro; or
  $C_7-C_9$ aralkyl substituted with halogen $C_1-C_4$ alkyl, trihalomethyl, $C_1-C_4$ alkoxy, trihalomethoxy, trihalomethylthio, $C_1-C_4$ alkylthio, phenyl, phenoxy, cyano or nitro;
$R^1$ is
  hydrogen,
  $C_1-C_3$ alkyl,
  $C_7-C_9$ aralkyl,
  phenyl,
  $C_7-C_9$ aralkyl substituted with halogen, $C_1-C_4$ alkyl, trihalomethyl, $C_1-C_4$ alkoxy, trihalomethoxy, trihalomethylthio, $C_1-C_4$ alkylthio, phenyl, phenoxy, cyano or nitro, or phenyl substituted with halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro;

$R^2$ is halogen or a radical of the formula:

$$-S-\underset{\underset{ZR^4}{\diagdown}}{\overset{\overset{A}{\|}}{P}}-YR^3$$

wherein $R^3$ and $R^4$ are each independently $C_1$–$C_4$ alkyl; and

A, Y and Z are each independently oxygen or sulfur.

The compounds employed in the practice of this invention may be produced by reacting a substituted tetrazole with a substituted chloroacyl halide in accordance with the following reaction scheme:

$$\underset{H}{\overset{N=\!=\!=N}{R-\overset{\|}{\underset{N}{\diagup}}\diagdown N}} + R^1-\underset{\underset{}{|}}{\overset{Cl}{|}}CH-\overset{O}{\overset{\|}{C}}-X$$

$$\underset{O}{\overset{N-\!\!-\!\!-N}{R-\overset{\|}{\diagdown}\diagup}}\overset{R^1}{\underset{|}{\diagdown}}CH-X + HCl + N_2$$

wherein R and $R^1$ are as defined in formula I above; and X is halogen. Preferably, an excess of chloroacyl halide is employed. The reaction is typically performed in the presence of an inert solvent, such as xylene, and at a temperature of between about 100° and about 140° C. During the reaction period, the reactor should be subjected to an appropriate venting system in order to remove the nitrogen and hydrochloric acid byproducts.

The reaction product is typically isolated by first washing with a dilute basic solution (e.g., 0.01 N sodium hydroxide) and subsequently with water. The washed product is then generally subjected to drying to remove the water and traces of solvent.

In those cases wherein $R^2$ is halogen, X and $R^2$ are equivalent in the reaction scheme above. In those cases wherein $R^2$ is a thiophosphate moiety, the reaction product above is further reacted with a thiophosphate salt in accordance with the following reaction scheme:

$$\underset{O}{\overset{N-\!\!-\!\!-N}{R-\overset{\|}{\diagdown}\diagup}}\overset{R^1}{\underset{|}{\diagdown}}CH-X + M-S-\underset{\underset{ZR^4}{\diagdown}}{\overset{\overset{A}{\|}}{P}}-YR^3$$

wherein R, $R^1$, $R^3$, $R^4$, A, Y and Z are as defined in formula I above; X is halogen; and M is an alkali metal ion or ammonium. Preferably, an excess of thiophosphate salt is employed. This reaction is typically conducted in the presence of an inert solvent, such as acetone or acetonitrile, at between about 10° and about 70° C.

The product is typically isolated by removing the solvent (generally under reduced pressure) and extracting the residue with a polychlorinated hydrocarbon, such as dichloromethane or chloroform. The product is then typically washed, first with a dilute acid solution (e.g., 0.0 1N hydrochloric acid) and subsequently with water; followed by drying.

The tetrazole starting materials may be produced in accordance with the method disclosed by W. G. Finnegan et al, "An Improved Synthesis of 5-Substituted Tetrazoles", Journal of the American Chemical Society, Vol. 80, pp. 3908–3911 (1958), while the substituted chloroacyl halides and thiophosphate salts are compounds well known to those in the synthesis art.

The compounds employed in the method of this invention are of the formula:

$$\underset{O}{\overset{N-\!\!-\!\!-N}{R-\overset{\|}{\diagdown}\diagup}}\overset{R^1}{\underset{|}{\diagdown}}CH-R^2$$

wherein:
R is
  $C_1$–$C_{12}$ alkyl,
  $C_3$–$C_6$ cycloalkyl,
  $C_3$–$C_6$ cycloalkyl substituted with one or more members selected from the group consisting of halogen and $C_1$–$C_3$ alkyl,
  allyl,
  $C_3$–$C_5$ alkoxycarbonylmethyl,
  $C_7$–$C_9$ aralkyl,
  styryl,
  phenyl,
  naphthyl,
  furanyl,
  pyridyl,
  thienyl,
  phenyl substituted with halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro; or
  $C_7$–$C_9$ aralkyl substituted with halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro;

$R^1$ is
  hydrogen,
  $C_1$–$C_3$ alkyl,
  $C_7$–$C_9$ aralkyl,
  phenyl,
  $C_7$–$C_9$ aralkyl substituted with halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro, or
  phenyl substituted with halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro;

$R^2$ is halogen or a radical of the formula:

$$-S-\underset{\underset{ZR^4}{\diagdown}}{\overset{\overset{A}{\|}}{P}}-YR^3$$

wherein $R^3$ and $R^4$ are each independently $C_1$–$C_4$ alkyl; and A, Y and Z are each independently oxygen or sulfur.

Preferably,
R is
  $C_1$–$C_6$ alkyl,
  cyclopropyl, cyclopropyl substituted with one or more members selected from the group consisting of chlorine and methyl,
pyridyl,
thienyl,
phenyl,
phenyl substituted with chlorine, $C_1$–$C_3$ alkyl, trihalomethyl, $C_1$–$C_3$ alkoxy or nitro,
benzyl, or
benzyl substituted with chlorine, $C_1$–$C_3$ alkyl, trihalomethyl, $C_1$–$C_3$ alkoxy or nitro;
$R^1$ is
hydrogen,
$C_1$–$C_3$ alkyl,
phenyl,
phenyl substituted with chlorine, fluorine or $C_1$–$C_3$ alkyl,
benzyl, or
benzyl substituted with chlorine, fluorine or $C_1$–$C_3$ alkyl;
$R^2$ is chlorine, or a radical of the formula

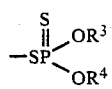

wherein $R^3$ and $R^4$ are each independently $C_1$–$C_3$ alkyl.

The compounds employed in the method of this invention are typically utilized in the form of a composition comprised of (a) chemical (i.e., a substituted 1,3,4-oxadiazole); and (b) a suitable carrier.

To prepare such agriculturally useful compositions, the substituted 1,3,4-oxadiazole may be mixed with an adjuvant to provide compositions in the form of finely-divided particulate solids, granules, pellets, wettable powders, flowable liquids, soluble powders, solutions, and aqueous or organic solvent dispersions or emulsions. Such formulations may be of several different physical and chemical types, any of which could be made by one familiar with the art. For instance, the agriculturally active compound may be impregnated on finely-divided or granular inorganic or organic carriers such as attapulgite clay, sand, vermiculite, corn cob, activated carbon or other granular carriers known to the art. The impregnated granules may then be spread on the soil or incorporated into the soil.

Alternatively, the chemical may be formulated as a wettable powder by grinding it into a fine powder and mixing it with an inactive powdered carrier to which a surface active dispersing agent has been added. Typical powdered solid carriers are the various mineral silicates (such as mica, talc, pyrophyllite, clays and the like) or powdered organic material (e.g., corn cob). The wettable powder may then be dispersed in water and sprayed on the soil surface, or on crop or weed plants. Alternatively, such powders could be applied directly to crop plant seeds as seed coatings.

Similarly, an emulsifiable concentrate may be prepared by dissolving the chemical in a solvent such as benzene, toluene, or other aliphatic or aromatic hydrocarbon to which a surface active dispersing agent generally has been added. The emulsifiable concentrate may then be dispersed in water and applied by spraying.

The concentration of active chemical in the composition may vary widely typically ranging from about 0.1 to about 95% by weight. The concentration of active chemical in dispersions applied to the soil, seed or foliage is typically between about 0.002% and about 80% by weight.

Formulations containing the active ingredient(s) may be dispersed in water or an organic liquid (such as oil) and applied to target plants. Surface active agents may be added to the applied solution to increase its qualitative or quantitative range of activity. Suitable surface active agents are well known to those skilled in the art. Reference may be made to McCutcheon's Detergents and Emulsifiers (1980, Allured Publ. Co., Ridgewood, N.J.) for examples of appropriate surface active agents. Similarly, such formulations may be applied to the soil either as a liquid or a granule.

The chemical is typically applied at a rate of from about 0.05 to about 25 pounds per acre (about 0.056 to about 28 kg/ha). However, the most suitable dosage of application, and the most effective type and amount of adjuvant substance will depend on a number of factors, including the plant species; the stage of plant development; the method of application; the specific biological effect desired; the air and soil temperature and the quantity and intensity of rainfall before and after treatment; the soil type, pH, fertility and moisture and organic matter content; the physiological condition and vigor of the target plants; the relative humidity and wind velocity of the air around the crop at the time of treatment; the extent and density of the foliar canopy of the target plant; the light quality, intensity and duration each day; the type and interval of previous and subsequent crop protectant chemical applications. However, one skilled in the art can, by routine experimentation, readily determine optimum conditions for the employment of any particular substituted 1,3,4-oxadiazole compound.

EXAMPLES

The following Examples are intended to further illustrate the invention and are not intended to limit the scope of the invention in any manner whatsoever.

EXAMPLE 1

Production of 2-(2,2-dichloro-1-methylcyclopropyl)-5-(1-(0,0-diethyldithiophosphoryl)ethyl)-1,3,4-oxadiazole (Compound Number 37)

3.2 grams of 2-(2,2-dichloro-1-methylcyclopropyl-5-(1-chlorethyl)-1,3,4-oxadiazole (0.01 mole) and 2.8 grams of the ammonium salt of 0,0-diethyldithiophosphate were reacted, under agitation, in 25 ml of acetone at 40°–50° C. for thirty minutes. After stirring overnight at ambient temperature, the precipitated salt was filtered off and the filtrate reduced to an oil under vacuum. The amber oil was taken up in chloroform and washed twice with water, dried and again reduced under vacuum to 3.5 grams of an oil (86% of theoretical). The structure was verified by IR and NMR analyses.

EXAMPLE 2

Preparation of 2-(3-trifluorotolyl)-5-alpha-(0,0-diethyldithiophosphoryl)benzyl)-1,3,4-oxadiazole (Compound Number 18)

6.8 grams (0.02 mole) of 2-(3-trifluorotolyl)-5-(alpha-chlorobenzyl)-1,3,4-oxadiazole and 4.2 grams (0.021 mole) of the ammonium salt of 0,0-diethyldithiophosphate were reacted, under agitation, in 35–40 ml of acetonitrile at 50°-60° C. for two hours. The reaction product was stirred overnight at ambient temperature, and the precipitated salt was removed by filtration and the solvent under vacuum. The resulting oil was dissolved in 75 ml of chloroform and washed with three 80 ml portions of water. The chloroform layer was dried over anhydrous sodium sulfate and evaporated under vacuum, yielding 9 grams of product (92% of theoretical). The product of this preparation was verified by IR and NMR analyses.

EXAMPLE 3

Several 1,3,4-oxadiazolyl methylhalide compounds were prepared reacting the appropriate substituted tetrazole compound with the appropriate substituted chloroacyl chloride. These compounds are summarized in Table I below.

TABLE I

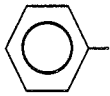

| Compound Number | R | $R^1$ |
|---|---|---|
| 2 | 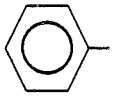 | 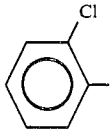 |
| 4 | 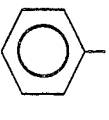 | 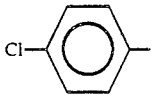 |

TABLE I-continued

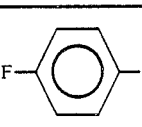

| Compound Number | R | $R^1$ |
|---|---|---|
| 11 | 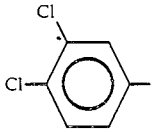 | 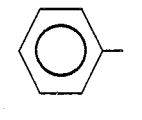 |
| 13 | 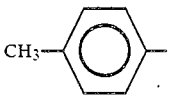 | 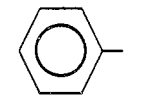 |
| 17 | 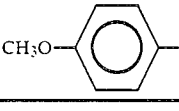 | 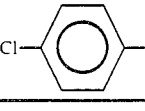 |
| 24 | 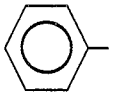 | 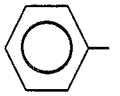 |

EXAMPLE 4

Employing a process similar to that employed in Examples 1 and 2, several 1,3,4-oxadiazolyl thiophosphate compounds were prepared. These compounds as well as those of Examples 1 and 2, are summarized in Table II below.

TABLE II

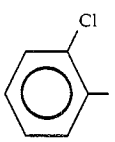

| Compound Number | R | $R^1$ | $R^3$ | $R^4$ | A | Y | Z |
|---|---|---|---|---|---|---|---|
| 1 | 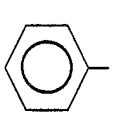 | 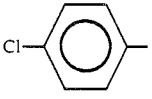 | $C_2H_5$ | $C_2H_5$ | S | O | O |
| 3 | 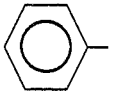 | 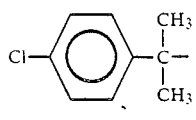 | $C_2H_5$ | $C_2H_5$ | S | O | O |
| 5 | 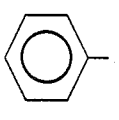 | 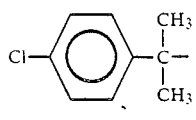 | $C_2H_5$ | $C_2H_5$ | S | O | O |
| 6 | 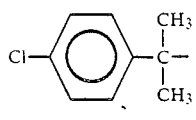 | 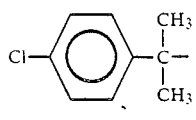 | $C_2H_5$ | $C_2H_5$ | S | O | O |

TABLE II-continued $$R-\underset{O}{\overset{N-N}{\underset{\|}{C}}}\underset{}{\overset{R^1}{\underset{|}{C}}}=CH-S-\underset{ZR^4}{\overset{A}{\underset{\|}{P}}}\underset{ZR^4}{\overset{YR^3}{}}$$

| Compound Number | R | R¹ | R³ | R⁴ | A | Y | Z |
|---|---|---|---|---|---|---|---|
| 7 | 4-Cl-C₆H₄- | C₆H₅- | CH₃ | CH₃ | S | O | O |
| 8 | 4-Cl-C₆H₄- | C₆H₅- | i-C₃H₇ | i-C₃H₇ | S | O | O |
| 9 | 4-Cl-C₆H₄- | C₆H₅- | C₄H₉ | C₄H₉ | S | O | O |
| 10 | 4-Cl-C₆H₄- | 4-F-C₆H₄- | C₂H₅ | C₂H₅ | S | O | O |
| 12 | 3,4-Cl₂-C₆H₃- | C₆H₅- | C₂H₅ | C₂H₅ | S | O | O |
| 14 | 2-CH₃-C₆H₄- | C₆H₅- | C₂H₅ | C₂H₅ | S | O | O |
| 15 | 3-CH₃-C₆H₄- | C₆H₅- | C₂H₅ | C₂H₅ | S | O | O |
| 16 | 4-CH₃-C₆H₄- | C₆H₅- | C₂H₅ | C₂H₅ | S | O | O |
| 18 | 2-CF₃-C₆H₄- | C₆H₅- | C₂H₅ | C₂H₅ | S | O | O |
| 19 | 3-CF₃-C₆H₄- | C₆H₅- | C₂H₅ | C₂H₅ | S | O | O |
| 20 | 3-CF₃-C₆H₄- | 4-F-C₆H₄- | C₂H₅ | C₂H₅ | S | O | O |

TABLE II-continued

Structure:
$$R-C(=O)-N=N-C(R^1)=... CH-S-P(=A)(YR^3)(ZR^4)$$

| Compound Number | R | R¹ | R³ | R⁴ | A | Y | Z |
|---|---|---|---|---|---|---|---|
| 21 | 4-CF₃-C₆H₄ | 4-F-C₆H₄ | C₄H₉ | C₄H₉ | S | O | O |
| 22 | 4-CH₃O-C₆H₄ | 4-Cl-C₆H₄ | C₂H₅ | C₂H₅ | S | O | O |
| 23 | 4-CH₃O-C₆H₄ | 4-Cl-C₆H₄ | i-C₃H₇ | i-C₃H₇ | S | O | O |
| 25 | 3,4,5-Cl₃-C₆H₂ | C₆H₅ | C₂H₅ | C₂H₅ | S | O | O |
| 26 | 4-NO₂-C₆H₄ | 4-Cl-C₆H₄ | C₂H₅ | C₂H₅ | S | O | O |
| 27 | 4-NO₂-C₆H₄ | 3,4-(CH₃)₂-C₆H₃ | C₂H₅ | C₂H₅ | S | O | O |
| 28 | 4-NO₂-C₆H₄ | 4-CH₃-C₆H₄ | C₂H₅ | C₂H₅ | S | O | O |
| 29 | 2,6-Cl₂-C₆H₃ | C₆H₅ | C₂H₅ | C₂H₅ | S | O | O |
| 30 | C₆H₅-CH(CH₃)- | C₆H₅ | C₂H₅ | C₂H₅ | S | O | O |
| 31 | 4-Cl-C₆H₄ | C₂H₅ | C₄H₉ | C₄H₉ | S | O | O |
| 32 | 4-CF₃-C₆H₄ | C₂H₅ | C₂H₅ | C₂H₅ | S | O | O |

TABLE II-continued $$R-\overset{N=N}{\underset{O}{\bigparallel}}\overset{R^1}{\underset{CH-S}{\bigparallel}}\overset{A}{\underset{ZR^4}{\overset{\parallel}{P}}}YR^3$$

| Compound Number | R | R¹ | R³ | R⁴ | A | Y | Z |
|---|---|---|---|---|---|---|---|
| 33 | pyrid-2-yl |  | i-C₃H₇ | i-C₃H₇ | S | O | O |
| 34 | pyrid-3-yl | H | C₂H₅ | C₂H₅ | S | O | O |
| 35 | thien-2-yl |  | C₂H₅ | C₂H₅ | S | O | O |
| 36 | 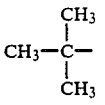 |  | C₂H₅ | C₂H₅ | S | O | O |
| 37 | 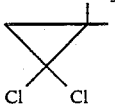 | CH₃ | C₂H₅ | C₂H₅ | S | O | O |
| 38 | 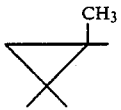 |  | C₂H₅ | C₂H₅ | S | O | O |
| 39 | 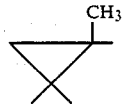 |  | i-C₃H₇ | i-C₃H₇ | S | O | O |

EXAMPLE 5

Stimulation of Growth in Stature in Soybean

To illustrate the effectiveness of the described compounds as growth stimulants for soybeans, 150 mg of chemical were dissolved in 5 ml of acetone to which 7.5 mg conventional emulsifying agent (e.g., ethoxylated sorbitan monolaurate, "Tween 20" [trademark]) was added. This solution was diluted to 50 ml with distilled water, thereby producing a 3000 ppm solution. Employing an air-pressured sprayer, the foliage of two-week-old soybean plants (Glycine max (L.) Merr. cv. Williams) was wetted with such solutions to the drip point. After one week in the greenhouse, the plants were scored for stimulation of vegetative growth by comparing the one week growth of the treated plants with that of controls sprayed with a similar formulation not containing 1,3,4-oxadiazole compound. The results of this test are summarized in Table III.

TABLE III

| Compound Number | Plant Height* |
|---|---|
| 1 | 107 |
| 2 | 109 |
| 3 | 116 |
| 4 | 107 |
| 5 | 136 |
| 6 | 143 |
| 7 | 114 |
| 8 | 147 |
| 9 | 137 |
| 10 | 106 |
| 11 | 126 |
| 12 | 115 |
| 13 | 107 |
| 14 | 119 |
| 15 | 118 |
| 16 | 113 |
| 17 | 122 |
| 18 | 117 |
| 19 | 105 |
| 20 | 116 |
| 21 | 113 |
| 22 | 120 |
| 23 | 114 |
| 24 | 160 |
| 25 | 111 |
| 26 | 121 |
| 27 | 107 |
| 28 | 121 |
| 29 | 109 |
| 30 | 110 |
| 31 | 137 |
| 32 | 105 |
| 33 | 120 |
| 34 | 110 |

TABLE III-continued

| Compound Number | Plant Height* |
| --- | --- |
| 35 | 106 |
| 36 | 114 |
| 37 | 105 |
| 38 | 107 |
| 39 | 107 |

*Plant height as a percentage of the control at one week after treatment.

EXAMPLE 6

Stimulation of Barley Growth

To further illustrate the effectiveness of the described compounds as plant growth stimulants, 3000 ppm solutions of such compounds were prepared as in Example 5. These solutions were similarly applied to the foliage of 8-day old barley plants (Hordeum vulgare L. cv. Herta), eight plants per 10 cm square plastic pot. After one week in the greenhouse, total plant height per pot (soil line to tip of longest leaf) was measured and the height of the treated plants relative to untreated controls calculated.

| Compound No. | Relative Height* |
| --- | --- |
| 5 | 123 |
| 6 | 104 |
| 8 | 113 |

*Based on control = 100

EXAMPLE 7

Foliage Treatment—Lettuce

To illustrate the growth stimulating activity of the subject compounds, 125 mg of compound No. 22 were dissolved in 10 ml acetone and diluted to 100 ml with distilled water containing 0.2% commercial emulsifying agent (ethoxylated sorbitan monolaurate, Tween 20 TM). Twenty milliliters of this 1250 ppm solution were diluted to 100 ml with water containing emulsifying agent to produce a 250 ppm solution. Similarly, a 50 ppm solution was also prepared. The chemical was applied to the foliage of lettuce (Lactuca sativa L., cv. Grand Rapids) grown in 15 cm diameter plastic pots. The chemical solutions were applied to the foliage by atomization with a sprayer, wetting the foliage to the drip point. The plants were treated twice, once when they had 4 leaves and again when they had 8 leaves. After three weeks in a controlled environment chamber (27° C. day, 13° C. night, 13.5 hour photoperiod), the plants were scored for height and fresh weight of above ground organs and the data calculated in terms of percentage of that of untreated control plants.

| Compound No. | Dosage (ppm a.i.*) | Height (% of control) | Fresh Weight (% of control) |
| --- | --- | --- | --- |
| 22 | 1250 | 169 | 124 |
|  | 250 | 127 | 124 |
|  | 50 | 127 | 112 |

*Active Ingredient

EXAMPLE 8

Foliar Treatment—Beans

To further illustrate the effectiveness of subject compounds as plant growth stimulants, 500 and 100 ppm solutions of compound No. 22 were prepared in a fashion similar to that described in Example 7. These solutions were applied to the foliage of pinto bean plants (Phaseolus vulgaris L.) in the field in a volume of about 200 l/ha about 1 or 2 days before full bloom. At harvest, plant heights were measured and the number and weight of pods per plants were determined. Control plants were not treated.

| Compound No. | Dosage (ppm a.i.*) | Height (cm) | Pod Number | Pod Weight (grams) |
| --- | --- | --- | --- | --- |
| 22 | 500 | 93.0 | 21.6 | 41.6 |
|  | 100 | 98.5 | 18.4 | 32.3 |
| Control (Untreated) | — | 87.9 | 18.9 | 32.7 |

*Active Ingredient

EXAMPLE 9

Seed Soak Treatment—Beans

To illustrate the effectiveness of the subject compounds as growth stimulants when applied as a seed soak, 500 and 100 ppm solutions of Compound No. 22 were prepared in a manner similar to that described in Example 7, except that no emulsifying agent was used. Pinto bean seed were soaked overnight (about 18 hrs.) in these solutions, removed and air dried, and hand planted in the field, according to normal practice. Control seeds were soaked overnight in water and similarly planted. At one week after planting, stand counts (plants per 10 row-feet) and plant heights were determined.

| Compound No. | Dosage (ppm a.i.*) | Height (cm) | Plant Stand |
| --- | --- | --- | --- |
| 22 | 500 | 9.7 | 37 |
|  | 100 | 7.4 | 37 |
| Control | — | 5.3 | 35 |

*Active Ingredient

EXAMPLE 10

Seed Treatment—Wheat

To illustrate the effectiveness of the subject compounds as seed treatments, 250 mg of test chemical were dissolved in 5 ml acetone. This solution was added dropwise to 50 g samples of wheat seeds (Triticum aestivum L. cv. Roland), which were swirled to assume uniform coverage of the seed coat. The seeds were then allowed to air dry. This treatment simulates a seed treatment dosage of 500 grams active ingredient per 100 kg seed. Similarly, 125 and 31 g/100 kg seed lots were also prepared. The seed were planted in amended soil in 15 cm diameter pots, 40 seeds per pot and placed in a greenhouse under ambient conditions. After 10 days, the pots were examined for percent emergence and for seedling height. The data obtained appear in Table IV.

TABLE IV

| Compound No. | Dosage (g/100 kg seed) | Germination (%) | Height (cm) |
| --- | --- | --- | --- |
| 5 | 500 | 97 | 16.0 |
|  | 125 | 100 | 15.7 |
|  | 31 | 97 | 15.7 |
| 6 | 500 | 97 | 16.5 |
|  | 125 | 100 | 16.0 |
|  | 31 | 93 | 16.0 |
| 22 | 500 | 93 | 16.2 |

TABLE IV-continued

| Compound No. | Dosage (g/100 kg seed) | Germination (%) | Height (cm) |
|---|---|---|---|
|  | 125 | 93 | 15.0 |
|  | 31 | 100 | 15.5 |
| 24 | 500 | 80 | 11.7 |
|  | 125 | 100 | 13.8 |
|  | 31 | 100 | 15.5 |
| Control (Untreated) | — | 75 | 13.6 |

The above data demonstrate the unexpectedly desirable plant growth stimulatory activity resulting from the method of this invention.

What is claimed is:

1. A method for stimulating the growth of plants, which method comprises applying directly to plant seeds prior to germination an effective plant growth stimulatory amount of a compound having the structural formula:

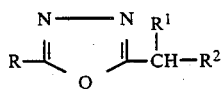

wherein:
R is
C$_1$-C$_{12}$ alkyl,
C$_3$-C$_6$ cycloalkyl,
C$_3$-C$_6$ cycloalkyl substituted with one or more members selected from the group consisting of halogen and C$_1$-C$_3$ alkyl,
allyl,
C$_3$-C$_5$ alkoxycarbonylmethyl,
C$_7$-C$_9$ aralkyl,
styryl,
phenyl,
naphthyl,
furanyl,
pyridyl,
thienyl,
phenyl substituted with halogen C$_1$-C$_4$ alkyl, trihalomethyl, C$_1$-C$_4$ alkoxy, trihalomethoxy, trihalomethylthio, C$_1$-C$_4$ alkylthio, phenyl, phenoxy, cyano or nitro; or
C$_7$-C$_9$ aralkyl substituted with halogen C$_1$-C$_4$ alkyl, trihalomethyl, C$_1$-C$_4$ alkoxy, trihalomethoxy, trihalomethylthio, C$_1$-C$_4$ alkylthio, phenyl, phenoxy, cyano or nitro;
R$^1$ is
hydrogen,
C$_1$-C$_3$ alkyl,
C$_7$-C$_9$ aralkyl,
phenyl,
C$_7$-C$_9$ aralkyl substituted with halogen, C$_1$-C$_4$ alkyl, trihalomethyl, C$_1$-C$_4$ alkoxy, trihalomethoxy, trihalomethylthio, C$_1$-C$_4$ alkylthio, phenyl, phenoxy, cyano or nitro, or
phenyl substituted with halogen, C$_1$-C$_4$ alkyl, trihalomethyl, C$_1$-C$_4$ alkoxy, trihalomethoxy, trihalomethylthio, C$_1$-C$_4$ alkylthio, phenyl, phenoxy, cyano or nitro;
R$^2$ is halogen or a radical of the formula:

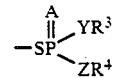

wherein R$^3$ and R$^4$ are each independently C$_1$-C$_4$ alkyl; and A, Y and Z are each independently oxygen or sulfur.

2. A method in accordance with claim 1 wherein:
R is
C$_1$-C$_6$ alkyl,
cyclopropyl,
cyclopropyl substituted with one or more members selected from the group consisting of chlorine and methyl,
pyridyl,
thienyl,
phenyl,
phenyl substituted with chlorine, C$_1$-C$_3$ alkyl, trihalomethyl, C$_1$-C$_3$ alkoxy or nitro,
benzyl, or
benzyl substituted with chlorine, C$_1$-C$_3$ alkyl, trihalomethyl, C$_1$-C$_3$ alkoxy or nitro;
R$^1$ is
hydrogen,
C$_1$-C$_3$ alkyl,
phenyl,
phenyl substituted with chlorine, fluorine or C$_1$-C$_3$ alkyl,
benzyl, or
benzyl substituted with chlorine, fluorine or C$_1$-C$_3$ alkyl;
R$^2$ is chlorine, or a radical of the formula

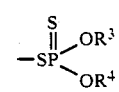

wherein R$^3$ and R$^4$ are each independently C$_1$-C$_3$ alkyl.

3. A method in accordance with claim 1 wherein said compound is applied at a rate of about 500 grams per 100 kg seed.

* * * * *